(12) United States Patent
Grau et al.

(10) Patent No.: US 6,705,719 B2
(45) Date of Patent: Mar. 16, 2004

(54) SIGHT PIECE, IN PARTICULAR FOR SKIING GOGGLES AND METHOD FOR THE MANUFACTURE THEREOF

(75) Inventors: Werner Grau, Haberskirch (DE); Franz Huber, Lam (DE)

(73) Assignee: Uvex Sports GmbH & Co. KG, Fürth (DE)

( * ) Notice: Subject to any disclaimer, the term of this patent is extended or adjusted under 35 U.S.C. 154(b) by 1 day.

(21) Appl. No.: 10/206,668

(22) Filed: Jul. 29, 2002

(65) Prior Publication Data

US 2003/0019017 A1 Jan. 30, 2003

(30) Foreign Application Priority Data

Jul. 27, 2001 (DE) .......................... 101 36 806

(51) Int. Cl.⁷ ............................................. G02C 13/00
(52) U.S. Cl. ........................................ 351/41; 351/178
(58) Field of Search ..................... 351/41, 44, 159, 351/178

(56) References Cited

U.S. PATENT DOCUMENTS 5,949,514 A * 9/1999 Wargon .................. 351/41
6,224,206 B1 * 5/2001 Schwartz ................. 351/44
6,530,659 B1 * 3/2003 Marcum .................. 351/41

FOREIGN PATENT DOCUMENTS

| AT | 406 448 B | 5/2000 |
| DE | 36 35 703 A1 | 4/1988 |
| DE | 86 28 009 U1 | 6/1988 |
| DE | 295 01 546 U1 | 4/1995 |
| DE | 295 16 680 U1 | 2/1996 |

OTHER PUBLICATIONS

Patent Abstracts of Japan, Publication No. 11079797, Publication Date, Mar. 23, 1999, Inventor Shibuya Takashi et al., Title: "Double Glazing".

Patent Abstracts of Japan, Publication No. 008697A, Publication date.Mar. 31, 1997, Inventor: Yamamoto Nobuyoshi et al.

* cited by examiner

*Primary Examiner*—Huy Mai
(74) *Attorney, Agent, or Firm*—Browdy and Neimark, P.L.L.C.

(57) ABSTRACT

In a sight piece, in particular for skiing goggles or the like, comprising a distal and a proximal sheet united by a flexible seal and spacer element that encircles along the edge, it is provided that the sheets are glued together by means of the seal and spacer element without the use of additional adhesive.

10 Claims, 1 Drawing Sheet

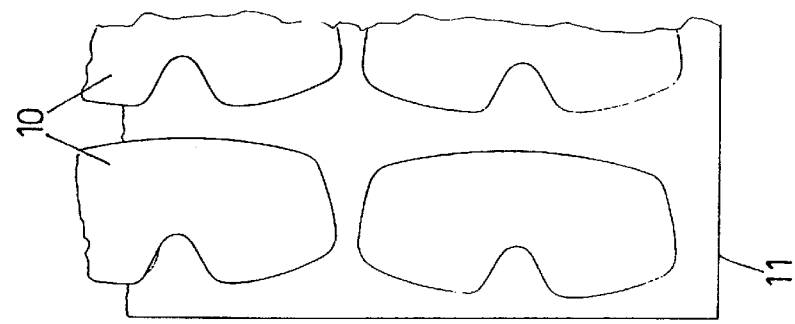
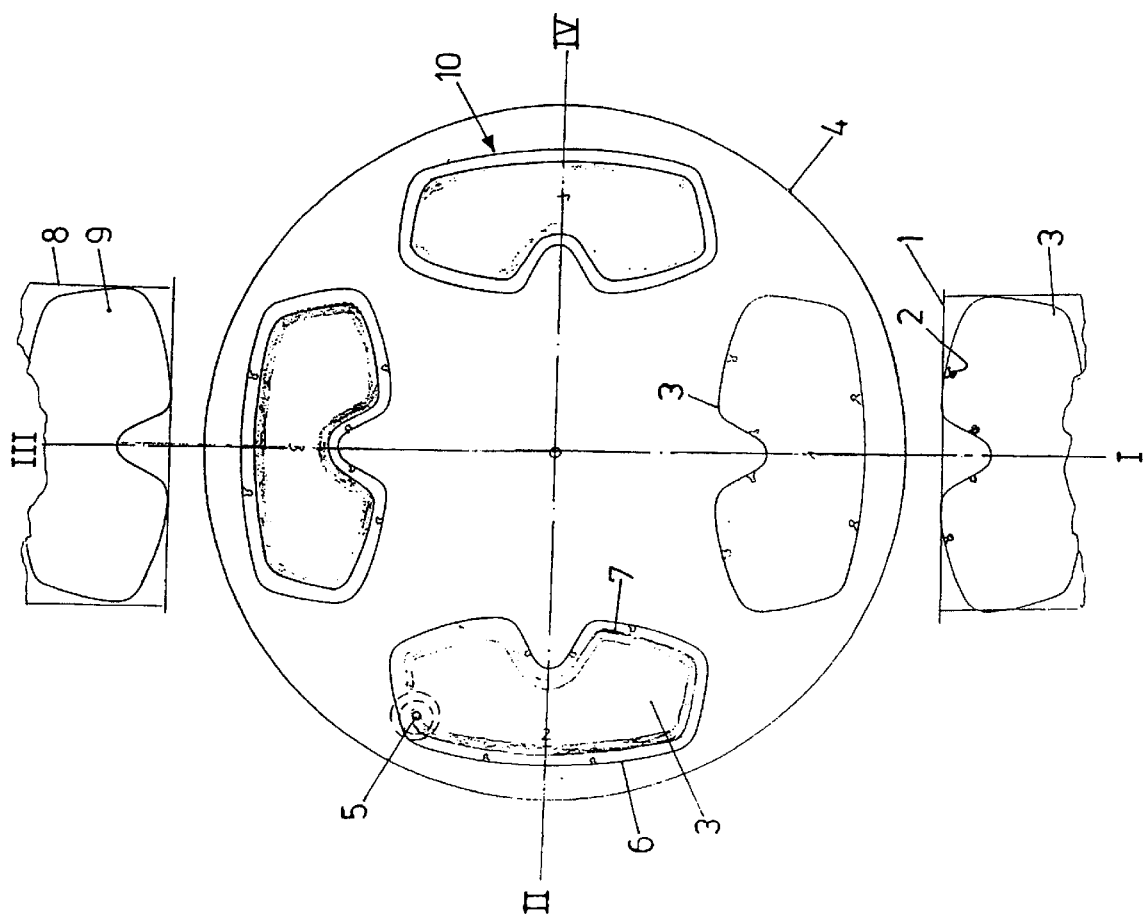

SIGHT PIECE, IN PARTICULAR FOR SKIING GOGGLES AND METHOD FOR THE MANUFACTURE THEREOF

BACKGROUND OF THE INVENTION

1. Field of the Invention

The invention relates to a sight piece, in particular for skiing goggles or the like, comprising a distal and a proximal sheet joined to each other by a flexible seal and spacer element that encircles along the edge.

2. Background Art

So-called double sight pieces of the generic type have been known for a long time from skiing goggles and motorbike helmet visors. They enable varying materials to be used for the proximal and distal sheets i.e., an especially scratchproof material for the distal sheet and a material appropriate for antimist coating in the case of the proximal sheet. The enclosed air cushion also counteracts sight piece fogging.

Various techniques or injection molding have been familiar methods for the manufacture of double sight piece arrangements of the generic type. For example, the distal sheet is produced by deep drawing, with an outer edge being formed that projects from the virtual plane of the sheet; the proximal sheet is then fixed to this edge by gluing or ultrasonic welding. Deep drawing or injection molding the distal sheet is costly and the bond that originates is extraordinarily rigid. As opposed to this, sight pieces of skiing goggles need to be as elastic and flexible as possible for injuries and fragmenting to be avoided in the case of skiing accidents.

It has further been known to punch the material of the seal and spacer element from flat-spread material, in particular foam material, and then to glue the sheets together by means of an adhesive. Punching produces a considerable amount of waste and glue-bonding is rather labor-consuming.

DE 295 16 680 U 1 teaches to apply the two components of a polyurethane foam along the outer edge of a sight piece for skiing goggles in a manner numerically controlled, producing a foam strip that bears against a wearer's face.

JP patent abstracts 11 079 797 A and 09 086 979 A disclose to mount a seal of hydrocarbon resin or partially vulcanized butyl rubber between two plane-parallel glass sheets.

SUMMARY OF THE INVENTION

Proceeding from this, it is the object of the invention to further develop a sight piece of the type mentioned at the outset in such a way that it has advantageous functional properties and an attractive optical appearance accompanied with the capability of rapid manufacture at a low cost.

According to the invention, this object is attained by the sheets being glued together by means of the seal and spacer element without utilization of additional glue.

This is preferably put into practice by the seal and spacer element consisting of a flexible silicone based sealant or of a polyurethane based sealant that is sprayed on one of the two sheets and, after placement of the second sheet, simultaneously used for gluing the sheets together.

The flexible silicone based sealant is preferably formed on the basis of a silicone rubber acetate system. Such a material is distinguished by great flexibility, which is of major importance for the residing flexibility of the composite sheets.

By advantage, the silicone based sealant has a density of approximately 1.0 g/ml and/or a Shore hardness A of approximately 20 and/or a permissible overall deformation of approximately 25 percent and/or a retroactivity greater than 98 percent.

The polyurethane based sealant advantageously has a density of approximately 1 $g/cm^3$ and/or a hardness of approximately 1 Shore A and/or a viscosity of 10,500 mPa.

The distal sheet may, in a manner known per se, consist of cellulose propionate, cellulose acetate or polycarbonate and the proximal sight piece may consist of cellulose propionate or cellulose acetate or polycarbonate like-wise in a manner known per se.

The proximal sheet may be provided with an antimist coating on both sides. Conventional gluing techniques manage to place only a unilateral coating, which renders manufacturing at lot more complicated. The design according to the invention provides for stable bonding even with bilateral coating.

Manufacturing a sight piece according to the invention is put into practice by a method in which an encircling strand of the material of the seal and spacer element is placed by means of a nozzle on one of the two sheets that will form the later double sight piece and then, with the material still soft, the second sheet is positioned and pressed on so that, after curing, the seal and spacer element will form, having the desired shape and thickness and uniting the two sheets.

Preferably, the strand of the material that constitutes the seal and spacer element is applied by a CNC-controlled spray nozzle.

In keeping with a favorable embodiment, this may be put into practice by sight piece manufacture taking place on a turntable that rotates intermittently by 90° such that a first sheet, in particular the distal sheet, is taken from a depot and placed on the turntable; the turntable is then rotated by 90° into a second position; the material of the seal and spacer element is applied by means of a CNC-controlled nozzle in this second position; the turntable is then rotated by 90° into a third position in which the second sheet, in particular the proximal sheet, is taken from a depot and placed on the soft material of the seal and spacer element by defined pressure for a defined thickness of the seal and spacer element to form; the turntable is then moved into a fourth position from which the finished sight piece is discharged into a storing depot.

Details of the invention will become apparent from the ensuing description of a preferred embodiment, taken in conjunction with the drawing.

BRIEF DESCRIPTION OF THE DRAWING

The drawing is a diagrammatic plan view illustrating the manufacture of goggles according to the invention.

DESCRIPTION OF THE PREFERRED EMBODIMENT

A punched out sheet 3, which is provided with so-called keyholes 2 for subsequent mounting on a skiing goggles frame, is taken from a supply depot 1; it will constitute the distal sheet and is placed in a first position I on a turntable 4 that is intermittently rotatable by 90° at a time.

The turntable is then rotated by 90° into a second position II where pourable plastic is sprayed on along, and at a distance from, the outer edge 6 of the distal sheet 3, forming a seal and spacer element 7.

While the sprayed bead is still plastic and deformable, the turntable 4 is rotated by 90° into a third position III where the second punched out sheet 9, which will be the proximal sheet, is taken from a depot 8 and pressed by defined pressure on the first sheet 3 so that the plastically deformable bead sprayed thereon is deformed with two plane-parallel frontal faces resulting. The seal and spacer element 7 thus formed simultaneously works as a kind of adhesive for uniting the proximal sheet 3 and the distal sheet 9, there being no need of applying any additional adhesive.

Then finished sight piece 10 is removed in a fourth position IV rotated by another 90° and deposited in a storing depot 11.

The distal sheet 3 consists of polycarbonate, having a scratchproof coating. The proximal sheet consists of cellulose propionate and has an antimist coating on both sides.

The seal and spacer element consists of a one-component sealant on the basis of silicone rubber of a silicone rubber acetate system. When cured, this material possesses high flexibility.

The cured seal and spacer element has the following properties:

density: 1.0 g/ml skinning time: approximately 10 to 15 minutes

Shore hardness A: approximately 20 tensile stress at 100% elongation: approximately 0.4 N/mm$^2$ temperature resistance: −40° C. to +180° C.

Permissible overall deformation: 25% retroactivity: >98%

What is claimed is:

1. A sight piece, in particular for skiing goggles comprising a distal sheet and a proximal sheet which are united by a flexible seal and spacer element that encircles along the edge, wherein the sheets (3, 9) are glued together by the seal and spacer element (7) without use of additional adhesive.

2. A sight piece according to claim 1, wherein the seal and spacer element (7) consists of a flexible silicone sealant.

3. A sight piece according to claim 2, wherein the seal and spacer element (7) consists of a flexible silicone sealant on the basis of a silicone rubber acetate system or of a polyurethane based sealant.

4. A sight piece according to claim 3, wherein the silicone sealant has a density of approximately 1.0 g/ml or a Shore hardness A of approximately 20 or a permissible overall deformation of approximately 25% or a retroactivity >98%.

5. A sight piece according to claim 3, wherein the polyurethane based sealant has a density of approximately 1.0 g/cm$^3$ or a hardness of approximately 1 Shore A or a viscosity of approximately 10,500 mPa.

6. A sight piece according to claim 1, wherein the distal sheet (3) consists of one of cellulose propionate, cellulose acetate and polycarbonate and the proximal sheet (9) of one of cellulose propionate and cellulose acetate.

7. A sight piece according to claim 6, wherein the proximal sheet 9 is provided with an antimist coating on both sides.

8. A method for the manufacture of a sight piece, in particular for skiing goggles comprising a distal sheet and a proximal sheet which are united by a flexible seal and spacer element that encircles along the edge, wherein, on one of the two sheets of the later double sight piece, an encircling strand of the material of the seal and spacer element is applied by means of a nozzle and wherein, with the material still soft, the second sheet is then positioned and placed on such that, after curing, the seal and spacer element of predetermined shape and thickness forms, uniting the two sheets.

9. A method for the manufacture of a sight piece according to claim 8, wherein the strand of the material of the seal and spacer element is applied by a CNC-controlled spray nozzle.

10. A method for the manufacture of a sight piece according to claim 8, wherein manufacturing the sight piece takes place on a turntable which rotates intermittently by 90° at a time so that a first sheet, in particular the distal sheet, is taken from a depot and positioned on the turntable; the turn-table is rotated by 90° into a second position; in this second position, the material of the seal and spacer element is applied by a CNC-controlled nozzle; the turntable is then rotated by 90° into a third position, in which the second sheet, in particular the proximal sheet, is taken from a depot and placed on the soft material of the seal and spacer element by defined pressure for a defined thickness of the seal and spacer element to form; the turntable is then moved into a fourth position from which the finished sight piece is discharged into a storing depot.

* * * * *